United States Patent
Bertsch et al.

(10) Patent No.: US 9,842,304 B2
(45) Date of Patent: Dec. 12, 2017

(54) NETWORK SYSTEM FOR LOCATION-INDEPENDENT ACCESS TO A WORKLIST

(71) Applicant: SIEMENS AKTIENGESELLSCHAFT, Munich (DE)

(72) Inventors: Rüdiger Bertsch, Erlangen (DE); Vladyslav Ukis, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 520 days.

(21) Appl. No.: 13/874,576

(22) Filed: May 1, 2013

(65) Prior Publication Data
US 2014/0089005 A1    Mar. 27, 2014

(30) Foreign Application Priority Data
Sep. 27, 2012    (DE) .................. 10 2012 217 551

(51) Int. Cl.
*G06Q 50/00*    (2012.01)
*G06Q 10/06*    (2012.01)
*G06Q 50/24*    (2012.01)

(52) U.S. Cl.
CPC ......... *G06Q 10/0631* (2013.01); *G06Q 50/24* (2013.01)

(58) Field of Classification Search
CPC ............................... G06Q 50/22; G06Q 50/24
See application file for complete search history.

(56) References Cited

U.S. PATENT DOCUMENTS

| | | | | |
|---|---|---|---|---|
| 8,473,598 B1* | 6/2013 | Piper | ............................ | 709/223 |
| 2006/0109811 A1* | 5/2006 | Schotten et al. | .............. | 370/328 |
| 2009/0191878 A1* | 7/2009 | Hedqvist | ............... | H04W 36/32 455/441 |
| 2010/0332629 A1* | 12/2010 | Cotugno | ............... | G06F 9/5072 709/221 |

(Continued)

FOREIGN PATENT DOCUMENTS

WO    WO 2009058901 A2    5/2009

OTHER PUBLICATIONS

Teradici; "PCoIP technology explained. 2012"; URL:http://www.teradici.com/pcoip-technology.php; archiviert in www.archive.org am Sep. 20, 2012 (abgerufen am Jan. 21, 2016).; 2012.

(Continued)

*Primary Examiner* — Lena Najarian
(74) *Attorney, Agent, or Firm* — Harness, Dickey & Pierce, P.L.C.

(57) ABSTRACT

A network system and a method are disclosed for accessing functionalities or medical data within the framework of a diagnostic findings process. An on-premises server farm, a data center and a plurality of mobile terminal devices are provided for that purpose. The on-premises system is connected to the data center via a local network connection. The mobile network devices are connected to the data center via a mobile communications connection. The data center is a virtualization of the local on-premises server farm. The mobile communications connection to the data exchange is activated as soon as the mobile device leaves the transmit and/or receive range of the respective hospital (off-premises).

20 Claims, 2 Drawing Sheets

(56) References Cited

U.S. PATENT DOCUMENTS

| | | | |
|---|---|---|---|
| 2011/0208837 A1* | 8/2011 | Sartori | 709/219 |
| 2012/0095779 A1* | 4/2012 | Wengrovitz | G06Q 50/24 705/3 |
| 2012/0157795 A1* | 6/2012 | Chiu et al. | 600/301 |
| 2012/0233668 A1* | 9/2012 | Leafe et al. | 726/4 |
| 2013/0110534 A1* | 5/2013 | Iasella | G06Q 50/22 705/2 |
| 2013/0115885 A1* | 5/2013 | Schmitt | A61B 5/0002 455/41.2 |

OTHER PUBLICATIONS

German Office Action dated Jan. 22, 2016 for Application No. DE 10 2012 217 551.2.

German Office Action dated Nov. 11, 2015 for Application No. DE 10 2012 217 551.2.

* cited by examiner

FIG 2

NETWORK SYSTEM FOR LOCATION-INDEPENDENT ACCESS TO A WORKLIST

PRIORITY STATEMENT

The present application hereby claims priority under 35 U.S.C. §119 to German patent application number DE 102012217551.2 filed Sep. 27, 2012, the entire contents of which are hereby incorporated herein by reference.

FIELD

At least one embodiment of the present invention generally lies in the fields of electronics and networking technology and relates in particular to the application field of (imaging) medical engineering with the use of mobile computer-based devices, such as smartphones or tablet computers for example.

BACKGROUND

A medical application that is installed in accordance with the current state of the art on the local information technology infrastructure (on-premises) of a medical institution is usually only available at the installation site. Access to the data and functions of the application is made possible for the users (generally the physicians) in the form of what are termed worklists. As a result of the local availability of the applications the worklists can only be processed on site (on-premises) in the institution.

As soon as the user leaves the respective institution the worklists remain on the local systems (on-premises) of the institution. Although the physicians possess mobile tablet devices such as e.g. iPads, when they leave the institution they cannot take the worklist and the associated application and data with them in order to process them on the mobile device.

This means that the worklist of contemporary systems also cannot automatically accompany the physician when he/she leaves his/her institution. A disadvantage of this rigid form of deployment is that the physician is constrained into working in an inefficient and inflexible manner. Instead of having the worklist and the application at hand wherever he/she may be and being able to perform diagnostic assessments independently of location and according to the time available, the physician must be located in his/her institution in order to be able to determine the findings.

Solutions enabling an application to be accessed also from an external location are known in the prior art. Thus, for example, there exists a product called "Expert-i" which enables an application to be used remotely. Good network connections are a prerequisite for these solutions in order to set up a VPN tunnel to the clinic and establish a connection to the application. Particularly with mobile devices such as e.g. iPads, such network connections cannot be taken for granted. Rather, a standard mobile communications connection to the internet, such as e.g. UMTS or GPRS, is to be assumed. With such connections, which vary in terms of quality over time, it is not possible to set up any reliable VPN tunnels in order to work efficiently with the application.

Another solution that is employed relatively frequently these days is the development of a new, additional application for mobile devices. Usually this includes only a fraction of the functionality of the original application. Accordingly, interpreting diagnostic findings on the mobile device is possible only with very severe limitations. Furthermore, substantial costs are incurred for the development of the new mobile application.

A transparent solution which enables the application to be used both on-premises and on-device independently of location, and with which at the same time the physician's worklist can be adapted according to location, does not exist at the present time.

SUMMARY

At least one embodiment of the present application at least one of improves, makes more flexible and/or simplifies the approach known hitherto. In particular in at least one embodiment, it is intended to be possible for medical functions or, more specifically, a respective worklist to be processed by mobile terminal devices even when the mobile communications connection exhibits varying quality (bandwidth) and no reliable VPN tunnels can be set up. It is furthermore aimed to be possible also for the entire functionality of an original application installed on-premises to be made available to mobile terminal devices.

In particular, a network system and a method are disclosed for accessing, within the framework of a medical process, functionalities and/or medical data that are installed and/or provided on a local on-premises server.

Embodiments of the invention is described hereinbelow with reference to the system. Embodiment variants cited in the description and alternative solutions having further features and advantages are also to be applied equally to the method and vice versa. Accordingly, the dependent claims that are formulated and/or described in relation to the system can also be applied to the method and vice versa. The respective functional features of the method are in this case implemented by means of corresponding microprocessor modules which are embodied to handle the respective functionality. For example, the method-related step of "storing a data record in a findings archive" can be implemented by means of a memory which is embodied for storing the respective data record (as diagnostic findings).

According to one embodiment, the present invention relates to a computer-implemented network system for accessing, within the framework of a medical process, functionalities and/or medical data that are installed and/or provided on a local on-premises server, comprising:
  a local on-premises server farm which is installed in a medical institution and makes the functionalities and/or the medical data available in the form of worklists for processing by connected clients
  a data center having a server farm which can be accessed by clients and wherein the server farm of the data center is a virtualization of the local on-premises server farm
  a plurality of mobile, computer-based terminal devices,
  wherein the local on-premises server farm and the data center communicate via a local network connection and the data exchange is automatically synchronized
  and wherein the data center and the respective terminal device communicate via a WAN network connection, in particular a mobile communications connection,
  and wherein each of the terminal devices is equipped with a trigger signal transmitter for automatically detecting if the terminal device leaves the transmit and receive range of the medical institution in order in this event to automatically activate the data exchange between the terminal device and the data center.

A further embodiment of the present invention relates to a method for operating a network system for a medical institution having a plurality of mobile terminal devices. For that purpose a local on-premises server farm is provided which is installed in a medical institution (hospital/clinic) and makes functionalities and/or medical data available in the form of worklists for processing by connected clients. Furthermore a data center having a server farm is provided, wherein the data center is intended for data exchange with the mobile terminal devices which act as clients of a hypervisor and wherein the server farm of the data center is a virtualization of the local on-premises server farm. The method comprises the following steps:

detecting a trigger signal which signals if the mobile terminal device leaves the transmit and receive range of the medical institution, and if a trigger signal is detected:
 activating the data connections between the respective terminal device and the data center,
 synchronizing the data center with the on-premises system in relation to the respective terminal device's worklist requiring to be processed. This is preferably implemented by sending relevant worklist-specific data records from the on-premises system to the data center,
wherein the data center is automatically synchronized with the local server farm if a trigger signal has been detected and wherein the local on-premises server farm and the data center communicate via a local network connection, and wherein the data center and the respective terminal device communicate via a WAN or WLAN network connection, in particular a mobile communications connection.

An embodiment of the invention also relates to a computer program product which can be loaded into a memory of a digital computer and comprises software routines (when run on the digital computer) by which the steps according to the aforementioned aspects are executed which are described in connection with the method. In this case the hypervisor can be operated as a software-only virtualization with provided operating system or use drivers of the data center operating system.

BRIEF DESCRIPTION OF THE DRAWINGS

The invention is described in more detail below together with further features, preferred and alternative embodiment variants and advantages associated therewith with reference to the drawings, in which.

The invention is explained in greater detail below in connection with the figures.

DETAILED DESCRIPTION OF THE EXAMPLE EMBODIMENTS

The present invention will be further described in detail in conjunction with the accompanying drawings and embodiments. It should be understood that the particular embodiments described herein are only used to illustrate the present invention but not to limit the present invention.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

According to one embodiment, the present invention relates to a computer-implemented network system for accessing, within the framework of a medical process, functionalities and/or medical data that are installed and/or provided on a local on-premises server, comprising:
 a local on-premises server farm which is installed in a medical institution and makes the functionalities and/or the medical data available in the form of worklists for processing by connected clients
 a data center having a server farm which can be accessed by clients and wherein the server farm of the data center is a virtualization of the local on-premises server farm
 a plurality of mobile, computer-based terminal devices,
wherein the local on-premises server farm and the data center communicate via a local network connection and the data exchange is automatically synchronized
and wherein the data center and the respective terminal device communicate via a WAN network connection, in particular a mobile communications connection,
and wherein each of the terminal devices is equipped with a trigger signal transmitter for automatically detecting if the terminal device leaves the transmit and receive range of the medical institution in order in this event to automatically activate the data exchange between the terminal device and the data center.

The terms used within the context of the present patent application are explained in more detail below.

The on-premises server farm is a computer system or network which has been implemented for or in an organizational structure, such as e.g. for a hospital or a hospital network.

The term "worklist" refers to electronic data processing processes within the context of study findings. Generally this relates to processes in respect of a study with completed findings or for which findings are to be prepared. The study typically includes image data that has been acquired using different medical imaging devices (MRT, PET, CT, US, etc.). A worklist can therefore be a list of studies and associated applications for preparing diagnostic findings.

The data center is likewise a server farm which is operated as an IaaS service (IaaS: Infrastructure as a Service). This can also be implemented as a cloud system outside of the LAN or WLAN range of the hospital as a central data center. It is, however, also possible to install the data center as an additional system inside the hospital.

The terminal devices are computer-based, mobile electronic devices, such as e.g. smartphones, tablet PCs or mobile telecommunications equipment which at least possess a mobile communications connection and therefore can be used independently of location and also outside of the hospital (and consequently off-premises). According to an alternative embodiment variant of the invention the terminal devices also have an internet connection.

According to an example embodiment variant of the invention the network connection between the data center and the mobile devices (connected to the network system) is based on a WAN network (WAN: Wide Area Network) or WLAN network (WLAN: Wireless Local Area Network). Different variants are conceivable for connecting the mobile devices to the data center. On the one hand a PCoIP protocol (PC over IP protocol) can be deployed if a hypervisor system is used for the virtualization. For example, the VMware network system can be used. This advantageously means that the mobile devices do not necessarily have to be connected to the data center via a DSL connection. Alternatively, other virtualization systems can be used, such as e.g. the product HDX from the company Citrix™, Santa Clara, Calif., United States. On the other hand web services can also be used or SOAP-based protocols can be deployed.

According to another advantageous embodiment variant of the invention, the network connection between the local on-premises server farm and the data center can be embodied as unidirectional. In this case data packets (generated on a mobile basis) are sent in one direction only, from the data center to the on-premises server farm. An https data connection is preferably used for that purpose so that the requisite precautionary security measures (based on provision of firewalls) can be complied with even without activation of an additional port. An important advantage of this solution thus lies in the fact that no additional precautionary security provisions need to be made in the hospital since in this case no additional systems access security-critical medical data from outside. The data transfer is advantageously triggered or initiated exclusively by the on-premises hospital system.

Alternatively, however, it is also possible to provide a bidirectional data connection in order also to send data records or results that are produced in the cloud to the on-premises system. In order to enable the mobile devices to be utilized with their full functionality even in the case of long latency times in respect of the data transfer and narrow bandwidth and supply them accordingly with data records, strategies can be employed which transfer only relevant data (e.g. only the actually modified screen contents) from the data center to the mobile devices.

Normally the results generated in the cloud or by way of the mobile terminal devices are forwarded to an archive system (findings archive) which can be accessed both by the on-premises system and by the data center system. In this embodiment variant the local on-premises server farm and the data center have at least one shared data archive which they can access using write and/or read commands.

According to a further advantageous embodiment of the invention the data center can be installed as a cloud-operated IaaS server farm and comprise at least one hypervisor system. The hypervisor system serves for virtualizing the on-premises server farm. The virtualization preferably comprises a server virtualization (application backends) and a client virtualization (application frontends). If no specific hardware is required (e.g. 3D graphics accelerator), only the software of the on-premises system will be virtualized. Toward that end the hypervisor runs on top of a guest operating system and provides virtual machines. The applications of the on-premises system are therefore virtualized on the server side.

According to another advantageous embodiment variant of the invention the trigger signal transmitter can be implemented as a GPS-based transmit and receive module. On an event- or time-driven basis the mobile device then sends its current position to the on-premises system, which can thereupon automatically detect whether the mobile device is still located within or is already located outside of the transmit and receive range of the hospital. Alternatively the current position data of the mobile device can also be requested by the central system (e.g. on-premises). Alternatively it can also be detected whether the device is located in the LAN or WLAN range of the on-premises system. In this case the mobile device can also find application and be used for determining findings from medical data records when the device is located within the hospital. Then, however, an automatic switchover of device operation to WLAN should be initiated in order to avoid disturbances to other medical devices due to mobile communications. The switchover can be made transparent by means of an additional switchover signal on the user interface.

According to a further embodiment variant, the data center includes an authentication module which is embodied for implementing access rights and access rules of the medical institution and applying same for access by or to the terminal device. The authentication module can be configured flexibly and the security rules can also be changed during operation.

A further embodiment of the present invention relates to a method for operating a network system for a medical institution having a plurality of mobile terminal devices. For that purpose a local on-premises server farm is provided which is installed in a medical institution (hospital/clinic) and makes functionalities and/or medical data available in the form of worklists for processing by connected clients. Furthermore a data center having a server farm is provided, wherein the data center is intended for data exchange with the mobile terminal devices which act as clients of a hypervisor and wherein the server farm of the data center is a virtualization of the local on-premises server farm. The method comprises the following steps:
  detecting a trigger signal which signals if the mobile terminal device leaves the transmit and receive range of the medical institution, and if a trigger signal is detected;
  activating the data connections between the respective terminal device and the data center,
  synchronizing the data center with the on-premises system in relation to the respective terminal device's worklist requiring to be processed. This is preferably implemented by sending relevant worklist-specific data records from the on-premises system to the data center,
wherein the data center is automatically synchronized with the local server farm if a trigger signal has been detected and wherein the local on-premises server farm and the data center communicate via a local network connection, and wherein the data center and the respective terminal device communicate via a WAN or WLAN network connection, in particular a mobile communications connection.

The trigger signal can be detected on the terminal device and/or in the data center or the local server farm.

According to another embodiment variant, the automatic synchronization is performed only as and when required and in particular after detection of the trigger signal. The synchronization is furthermore performed on a worklist-specific basis, in other words only for the data records that are relevant to the processing of the respective worklist. Further filter settings still can be defined here, dependent on configuration.

An embodiment of the invention also relates to a computer program product which can be loaded into a memory of a digital computer and comprises software routines by which the steps according to the aforementioned aspects are executed which are described in connection with the method. In this case the hypervisor can be operated as a software-only virtualization with provided operating system or use drivers of the data center operating system.

Figure 1:
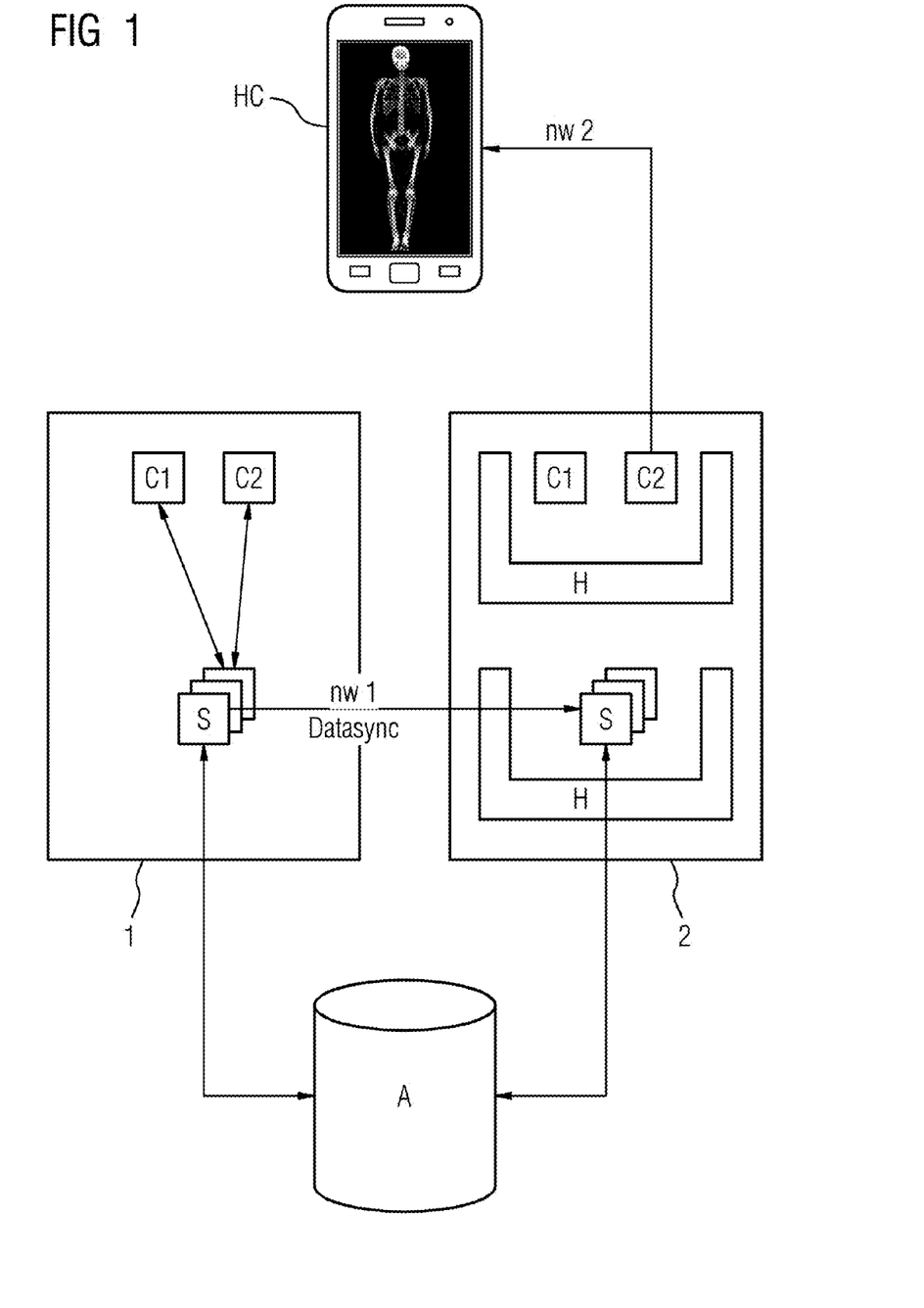
FIG. 1 is an overview-like illustration of a network system according to an example embodiment variant of the invention.

FIG. 1 shows in overview form the architecture or layout of the inventive network system, which basically comprises three main components:
  a local system which can be embodied as an on-premises server farm 1,
  a central data center 2, and
  a plurality of mobile electronic terminal devices D.

In addition the network system can include a long-term archive or data archive A in which medical studies or studies with diagnostic findings can be stored. Such an archive can be embodied as a conventional RAID system (RAID: Redundant Array of Independent Disks).

The data is preferably medical data that is relevant within the context of determining diagnostic findings. Usually the data records will include image datasets that have been acquired in the course of an imaging examination (e.g. using MRT, CT, PET, ultrasound, etc.). For the purpose of the diagnostic interpretation of the acquired image data or the study there exists a worklist which represents electronic processes for the data processing associated therewith. It is necessary to step through the worklist in order to arrive at the findings. Image annotations, filter settings, evaluations, text input, generation of medical reports and finding results can be included here, for example.

An important point is now to be seen in the fact that it should be possible during medical operation to accord the physician greater flexibility in his/her assessment and diagnostic activities. It is intended here that the task of preparing findings should not be confined to being performed only on permanently installed workstations within the hospital, but rather it should be possible to perform steps in the process also from mobile terminal devices D (such as e.g. smartphones or tablet PCs, etc.) if the physician is no longer located within the network range of the hospital. In order to process the worklist it is nonetheless necessary to access the relevant data records.

An embodiment of the invention resides in the on-premises system 1 which is implemented in the hospital additionally being "deployed" in a central data center 2. The data center 2 can likewise be embodied as a server farm. The server farm of the data center 2 can be deployed virtualized by means of a hypervisor or non-virtualized. Since the virtualization reduces the costs of the network overall and simplifies its administration, that solution is preferred. Depending on application in the medical image processing field it may be necessary to use special hardware (e.g. 3D graphics accelerator or mathematical co-processors); in this case it is not possible to virtualize the server farm completely. In the cases in which no special hardware is necessary, the clients of the server farm can be virtualized. The virtualization of the clients is necessary in order to enable virtual machines with full client application to be transferred by way of specific protocols to the actual client (the terminal device or device D). The client is usually the mobile terminal device D, which can be situated at an arbitrary location outside the network range of the local hospital.

Preferably the protocols employed for this are WAN-optimized. An example of such a protocol is the PCoIP protocol from VMware. This makes it possible to migrate the application out of the data center 2 and onto the terminal devices or devices which are connected to the data center 2 via a mobile communications connection.

The mobile devices D are basically connected to the data center 2 via a network connection nw2. The network connection nw2 is—as explained hereintofore—preferably a mobile communications connection. The network technology according to the invention is important because modern mobile devices D, such as e.g. iPads or Android tablets, normally have only conventional 3G/4G connections. A DSL connection between mobile device D and data center 2 cannot be taken for granted.

The on-premises server farm 1 is connected to the data center 2 via a network connection nw1 and sends medical studies to the data center 2 or, more specifically, the server farm of the same as and when required. This takes place whenever a device D leaves the hospital. The leaving of the hospital is detected by way of a trigger signal. For that purpose the network system includes a trigger signal transmitter T which is embodied in every terminal device D and serves for automatically detecting if the terminal device D moves out of the transmit and receive range of the medical institution. In this case, according to the invention, the data exchange between the terminal device D and the data center 2 will be activated automatically via the network connection nw2. Toward that end the data necessary for processing the physician's worklist is transmitted to the data center 2 so that the data will also be available on the physician's mobile device D.

As can be seen in FIG. 1, the data center 2 comprises a hypervisor system H. The hypervisor comprises a client hypervisor and/or a server hypervisor. The server hypervisor is merely optional, however, and is used for the virtualization of the server of the on-premises system 1 and in alternative embodiment variants of the invention may also not be implemented. A hypervisor H can also be understood as an administrator of virtual machines and serves inter alia for virtualizing the medical findings application which is installed locally in the clinic on-premises system 1. A (virtual) image of the physical on-premises computer 1 can therefore be generated which can then be made available to the mobile device D by way of the hypervisor H. Data and services are then, as usual, also available in the IaaS structure. Just snapshots or (changed or) relevant screen contents can also be transmitted here in order to save on data transfer costs. It is also possible to operate the computer of the hypervisor H for a plurality of virtual machines (e.g. for a plurality of applications of a clinical system or for a plurality of on-premises systems 1).

When the physician accesses a data record from the worklist on his/her device D, the client of the hypervisor H on the device D ensures that on the one hand the data can actually be retrieved from the hypervisor of the data center 2 and displayed on the mobile device D and on the other hand further configurations and/or filter settings can be used here which display the corresponding data on the device D e.g. only if the physician is located in the same country as the hospital. Otherwise access to the data is denied. This configuration is based on a security-related regulation that is intended to ensure that medical data records can only be accessed within the same country. No access to the data is to be possible from outside state boundaries.

It is, however, equally possible to specify other regulations and configurations so as to be able to change access flexibly also during operation of the network. Thus, for example, it is possible to define different configurations for different hospitals.

The position of the terminal device D is preferably established automatically by way of the trigger signal transmitter. The trigger signal transmitter T is based on an (assisted) GPS receiver arranged in the device D.

The on-premises server farm 1 and the data center 2 or, more specifically, the server farm of the data center 2 operate in a coordinated manner with a shared archive A in order to archive results of diagnostic findings or other data. It is also possible to access prior findings that are stored in the archive A.

According to an important point of an embodiment of the present invention, the data records of the on-premises system 1 and of the data center 2 are synchronized so that consistent administration of the physician's worklist can be ensured. Studies with completed findings are sent to the archive A by both server farms 1, 2. A study is only included in the physician's worklist in a server farm if it is not already available in the archive A.

If a study is stored both in the archive A and in one server farm, then it can be assumed on account of the network technology according to an embodiment of the invention that the study in the other server farm already includes findings and therefore can be removed or deleted from the server farm.

The network connection nw1 between on-premises system 1 and data center 2 is preferably an https connection. This is not mandatory, however. In alternative embodiment variants of the invention this can also be a local network connection (LAN or WLAN). In an embodiment variant this is embodied as unidirectional and is intended solely for transporting data from the on-premises system 1 to the data center 2. Alternatively it can also be a bidirectional data connection.

Specific medical protocols can be used within the hospital. Preferably the DICOM protocol (DICOM: Digital Imaging and Communications in Medicine) or HL7-based protocols will be used for transferring image data. Web services can also be used.

The network connection nw2 between the data center 2 and the respective devices D is a mobile communications connection and is based preferably on a PCoIP protocol in data exchange with the hypervisor system H. Alternative solutions provide a WAN (Wide Area Network) or WLAN (Wireless Local Area Network) network connection in this case.

Embodiments of the invention may lead to at least one of the following advantages.

Thanks to the inventive access method and/or network system, in at least one embodiment it is made possible for the physician to process his/her worklist completely independently of location and device using the same application from different devices (including also mobile devices D). The physician can use his/her mobile terminal device D and work with the same application that he/she also uses within the hospital. As a result the physician becomes independent of the PC or workstation at the hospital and can also access the necessary data outside of the hospital (e.g. at home or during a patient visit).

Inside the hospital the physician can work with the (permanently) installed diagnostic findings system in the customary way. On the other hand it is also possible for him/her to work on his/her mobile device D.

As soon as the physician leaves the hospital, he/she can also continue to process the worklist on his/her mobile device D. In this case the virtualized system from the data center 2 is used, with all necessary data records being automatically synchronized between on-premises system 1 and data center 2.

At the same time it is ensured that off-premises (i.e. outside of the hospital) the worklist will be filtered in accordance with the security and data protection guidelines. Possibly it can be configured that patient-specific data will not be displayed in the worklist if the physician leaves the country in which the hospital is located, since access to this patient data is only to be possible within the home country.

An authentication of the user is performed in data center 2 in order to ensure that access to patient data is administered as appropriate by the hospital. On-premises or locally on site, access rules and rights can be defined which govern access to data records by way of the mobile device D.

On his/her mobile device D, the physician enjoys the full functionality of the respective software application that he/she would also have within the hospital. This means that the physician can gain access to patient data via his/her worklist independently of location. The patient data can be automatically prefiltered so that diagnostic findings can essentially be determined at any position.

Figure 2:
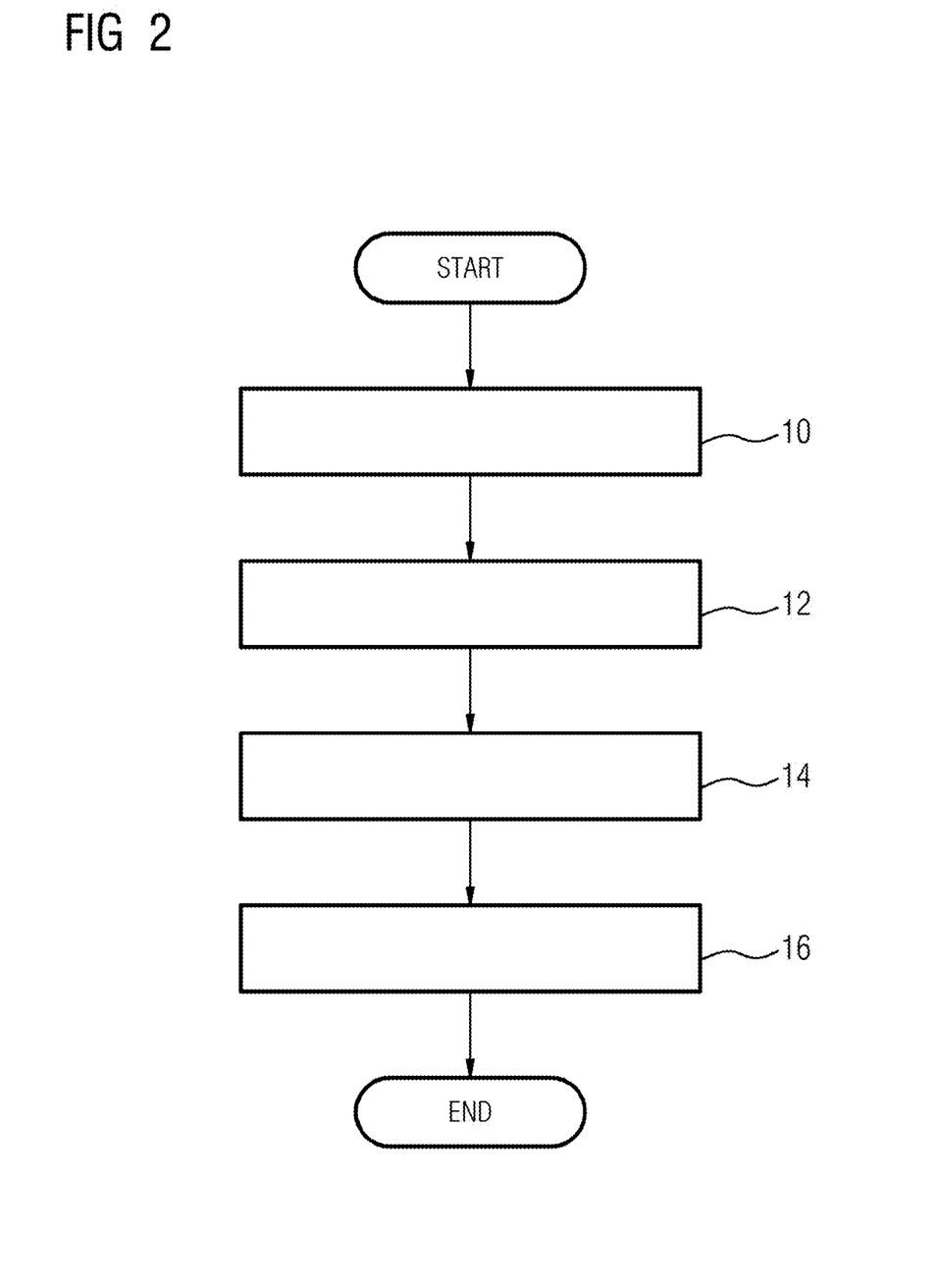
FIG. 2 is a flowchart of a method according to an example embodiment variant of the invention.

A typical workflow according to an example embodiment variant of the inventive method is described below with reference to FIG. 2. The method is based on the presupposition that a local on-premises server farm 1 and a data center 2 are provided, wherein the data center 2 is a virtualization of the local on-premises server farm 1.

After the start, a trigger signal is detected in step 10.

In step 12, the medical data record (preferably including image data) that is relevant to the findings process is sent from the on-premises system 1 to the data center 2.

In step 14, the network connection nw2 between terminal device D and data center 2 is activated.

In step 16, the data record is accessed from the mobile device D by way of the data center 2. The access can be a read and/or write access.

The method thereupon terminates.

The order in which the aforementioned method steps are performed is not mandatory and can also be varied. Thus, it is possible for example to perform steps 12 and 14 in a different order. Equally it is possible for steps 10 to 16 to be repeated iteratively.

The invention is fundamentally not limited to a specific device type (described in the present instance for a DICOM network as on-premises system comprising mobile terminal devices) or a specific type of telecommunications connections (e.g. mobile communication). It should furthermore be pointed out in this context that the basic concept of the invention is not limited to the examples described hereintofore and that equally variants of the disclosed examples may be derived by the person skilled in the art without leaving the scope of protection of the invention.

What is claimed is:

1. A network system, comprising:
   a local on-premises server farm, installed in a medical institution, the local on-premises server farm configured to make at least medical data available in a form of worklists for processing by connected clients connected via a local network connection associated with the medical institution such that the local on-premises server farm is not directly accessible outside of the local network connection;
   a mobile computer-based terminal device, the mobile computer-based terminal device being one of the connected clients, the mobile computer-based terminal device configured to,
     detect whether the terminal device moves outside of a transmit and receive range of the local network connection associated with the medical institution based on information from a global positioning system (GPS), and
     transmit a trigger signal, in response to the terminal device moving outside of the transmit and receive range; and
   a data center including a server farm having one or more processors configured to,
     automatically synchronize, via the local network connection, the medical data between the data center and the local on-premises server farm upon detection of the trigger signal such that the data center includes a virtualization of the local on-premises server farm,
     receive the trigger signal from the mobile computer-based terminal device, in response to the terminal device moving outside of a transmit and receive range of the local network connection associated with the medical institution, and
     activate a data exchange over a wide area network (WAN) network connection to transmit the medical data between the mobile computer-based terminal device and the data center in response to the trigger signal.

2. The network system of claim 1, wherein the WAN network connection is based on a PCoIP protocol.

3. The network system of claim 1, wherein the network connection between the local on-premises server farm and the data center is unidirectional.

4. The network system of claim 1, wherein the local on-premises server farm and the data center include at least one shared accessible data archive.

5. The network system of claim 1, wherein the data center is installed as a cloud-operated IaaS server farm and comprises at least one hypervisor system.

6. The network system of claim 1, wherein the virtualization comprises a server virtualization and a client virtualization.

7. The network system of claim 1, wherein the mobile computer-based terminal device transmits the trigger signal via the GPS.

8. The network system of claim 1, wherein the data center includes an authentication module, embodied to implement access rights and access rules of the medical institution and apply same for access by or to respective terminal devices.

9. A method for operating a network system for a medical institution including a plurality of mobile terminal devices, the method comprising:
   providing a local on-premises server farm, installed in the medical institution, to make at least medical data available in a form of worklists for processing by connected clients connected via a local network connection associated with the medical institution such that the local on-premises server farm is not directly accessible outside of the local network connection, the connected clients including a terminal device;
   providing a data center, including a server farm having one or more processors;
   receive, from the terminal device, a trigger signal in response to the terminal device moving outside of a transmit and receive range of the local network connection associated with the medical institution, the terminal device detecting whether the terminal device moves outside of the transmit and receive range based on information from a global positioning system (GPS);

automatically synchronizing, via the local network connection, the medical data between the data center and the local on-premises server farm upon detection of the trigger signal such that the data center includes a virtualization of the local on-premises server farm; and activating a data exchange over a wide area network (WAN) network connection to transmit the medical data between the terminal device and the data center in response to the trigger signal.

10. The method of claim 9, wherein the automatic synchronization is performed only as and when required.

11. The network system of claim 1, wherein the WAN network connection is a mobile communications connection.

12. The network system of claim 2, wherein the network connection between the local on-premises server farm and the data center is unidirectional.

13. The network system of claim 2, wherein the local on-premises server farm and the data center include at least one shared accessible data archive.

14. The network system of claim 2, wherein the data center is installed as a cloud-operated IaaS server farm and comprises at least one hypervisor system.

15. The network system of claim 2, wherein the virtualization comprises a server virtualization and a client virtualization.

16. The network system of claim 2, wherein the mobile computer-based terminal device transmits the trigger signal via the GPS.

17. The network system of claim 2, wherein the data center includes an authentication module, embodied to implement access rights and access rules of the medical institution and apply same for access by or to respective terminal devices.

18. The method of claim 9, wherein the WAN network connection is a mobile communications connection.

19. The method of claim 10, wherein the automatic synchronization is performed after detection of the trigger signal.

20. A non-transitory computer readable medium including a computer program product, loadable into a memory of a digital computer, comprising software routines that, when executed by the digital computer, configure the digital computer to, provide a local on-premises server farm, installed in a medical institution, to make at least medical data available in a form of worklists for processing by connected clients connected via a local network connection associated with the medical institution such that the local on-premises server farm is not directly accessible outside of the local network connection, the connected clients including a terminal device;

provide a data center, including a server farm having one or more processors;

receive, from the terminal device, a trigger signal in response to the terminal device moving outside of a transmit and receive range of the local network connection associated with the medical institution, the terminal device detecting whether the terminal device moves outside of the transmit and receive range based on information from a global positioning system (GPS);

automatically synchronize, via the local network connection, the medical data with the local on-premises server farm upon detection of the trigger signal such that the data center includes a virtualization of the local on-premises server farm; and activate a data exchange over a wide area network (WAN) network connection to transmit the medical data between the terminal device and the data center, in response to the trigger signal.

* * * * *